United States Patent [19]

Okuda et al.

[11] Patent Number: 4,997,423
[45] Date of Patent: Mar. 5, 1991

[54] LAMINATED SLIDING STOPPER FOR A SYRINGE

[75] Inventors: Tamotsu Okuda, Tokyo; Tomoyasu Muraki, Abiko, both of Japan

[73] Assignee: Daikyo Gomu Seiko Ltd., Tokyo, Japan

[21] Appl. No.: 366,279

[22] Filed: Jun. 14, 1989

Related U.S. Application Data

[63] Continuation of Ser. No. 244,633, Sep. 12, 1988, abandoned, which is a continuation of Ser. No. 105,132, Oct. 6, 1987, abandoned.

[30] Foreign Application Priority Data

Oct. 15, 1986 [JP] Japan ................... 61-243122

[51] Int. Cl.⁵ ............................................. A61M 5/315
[52] U.S. Cl. ..................................... 604/230; 604/218
[58] Field of Search ................ 604/230, 187, 218, 207

[56] References Cited

U.S. PATENT DOCUMENTS

| 2,607,342 | 8/1952 | Abel | 604/230 |
| 2,735,735 | 2/1956 | Abel | 604/230 |
| 3,628,523 | 12/1971 | Pirtle, Jr. | 604/187 X |
| 3,958,570 | 5/1976 | Vogelman et al. | 604/230 |
| 4,501,192 | 2/1985 | Knodel | 604/230 |

FOREIGN PATENT DOCUMENTS

| 141411 | 4/1980 | Fed. Rep. of Germany . |
| 19435 | 5/1977 | Japan . |
| 32602 | 8/1980 | Japan . |

Primary Examiner—John D. Yasko
Attorney, Agent, or Firm—Wenderoth, Lind & Ponack

[57] ABSTRACT

A laminated sliding stopper for a syringe, excellent in sliding or moving property and free from contamination of an injection liquid, is provided which consists of a rubber elastic body whose part to be contacted with the injection liquid and sliding part on the inner wall of the barrel are fully laminated with a film of tetrafluoroethylene.

6 Claims, 2 Drawing Sheets

4,997,423

LAMINATED SLIDING STOPPER FOR A SYRINGE

This application is a continuation of now abandoned application, Ser. No. 07/244,633 filed on Sept. 12, 1988, which is a continuation of now abandoned application, Ser. No. 07/105,132 filed on Oct. 6, 1987, now abandoned.

BACKGROUND OF THE INVENTION

1. Field of the Invention

This invention relates to a sliding or movable stopper or a piston of a syringe used for the hypodermic injection of liquid medicaments.

2. Description of the Prior Art

Syringes and generally constructed of a barrel and a plunger of glass slidably combined and of a barrel are a plunger rod provided, at the end thereof, with an elastic body of a rubber or thermoplastic elastomer, as a sealant, the barrel and plunger rod being of a resin such as polyethylene, polypropylene or polycarbonate. At the present time, this combination of a barrel and a sliding stopper consisting of a resin and rubber elastic body have most widely been used in the world. Of late, a syringe additionally serving as a container for a medicament has frequently been used in which the medicament is previously charged and sealed by a sliding stopper of a rubber elastic body.

For the purpose of preventing a medicament in a syringe from deterioration of the quality thereof due to a slidable stopper, there have been proposed a slidable stopper with a part, in contact with a liquid medicament, coated with a thin film of a fluoro-resin (Japanese Utility Model Publication No. 19435/1977), a sliding stopper consisting of a rubber laminated with polyethylene (hereinafter referred to as PE) or polypropylene (hereinafter referred to as PP) (Japanese Utility Model Publication No. 32602/1980) and a slidable stopper partly laminated with a fluoro-resin film (German Patent No. 3345351 A1). In any case, these proposals are directed to improvement of the chemical resistance of the stopper of a rubber elastic body and do not take the sliding property of the stopper into consideration.

Therefore, the sliding property of a rubber-like elastic body stopper is maintained by coating the inner wall of a barrel of a syringe and the stopper with s suitable quantity of silicone oil and silicone oil-free syringes for medicaments have not been available in the market.

SUMMARY OF THE INVENTION

It is an object of the present invention to provide a sliding stopper for a syringe used for the injection of a liquid medicament.

It is another object of the present invention to provide a movable piston or stopper for a syringe, consisting of a rubber body fully laminated with a film of tetrafluoroethylene resin.

It is a further object of the present invention to provide a sliding stopper whose position in a barrel can visually be confirmed by coating a colored tetrafluoroethylene film.

These objects can be attained by a sliding stopper for a syringe, consisting of a rubber elastic body whose part to be contacted with a liquid medicament and sliding part on the inner wall of the barrel are fully laminated with a film of tetrafluoroethylene resin.

DETAILED DESCRIPTION OF THE INVENTION

Of late, bad influences upon a human body due to foreign matters or fine particles in an injection medicament have been considered as a serious question in the field of medicines or medicaments and in U.S.A. and other countries, legislation has been made for the purpose of regulation of the influences (See USP XX[1], British Standards Institution 3236). Since the foreign matters or fine particles are mainly caused by silicone oils used as a lubricant for syringes, it has eagerly been desired to develop a syringe and medical instrument without using such a silicone oil.

In order to satisfy the above described need, the inventors have proposed sliding stoppers for syringes or syringes serving additionally as containers for liquid medicaments, laminated with tetrafluoroethylene-ethylene copolymer resins films (Japanese Patent Application Nos. 281083/1985 and 293070/1985). The present invention has been made to further improve these earlier inventions.

Accordingly, the present invention provides a sliding stopper or piston for a syringe, consisting of a rubber elastic body whose part to be contacted with a liquid medicament and sliding part on the inner wall of the barrel are completely laminated with a film of tetrafluoroethylene resin. In this specification, "stopper" is hereinafter used including the meaning of "piston".

In the preferred embodiments of the present invention, the film of tetrafluoroethylene resin (hereinafter referred to as TFE) has a thickness of 0.010 to 0.2 mm, the syringe additionally serves as a container for a medicament and the TFE film is colored, for example, in black.

Figures 1, 2:
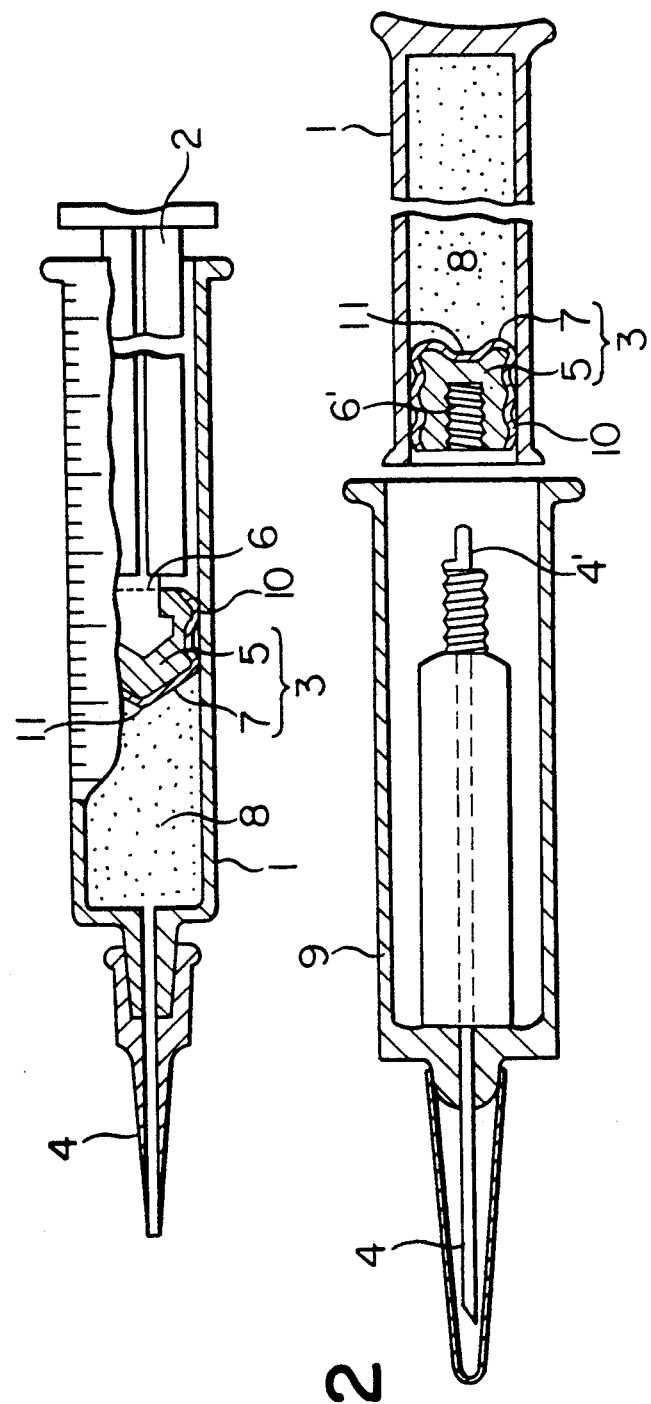
FIG. 1 is a cross-sectional view of one embodiment of the laminated rubber stopper of the present invention when applied to a syringe of disposable type.
FIG. 2 is a cross-sectional view of another embodiment of the laminated rubber stopper of the present invention when applied to a syringe additionally serving as a container.

As shown in FIG. 1, the feature of the present invention consists in a sliding stopper 3 consisting of a rubber base material 5 and a laminated part 7 with a TFE film on the surface thereof, in which the TFE laminated part 7 is provided on not only a part 11 to be contacted with a liquid medicament 8 but also a sliding part 10 on the inner wall of a barrel 1 of a syringe, whereby the coating of a silicone oil, as commonly effected in the prior art, is not necessary and deterioration of a medicament can be prevented.

When a colored TFE film is laminated in the sliding rubber stopper of the present invention, the position of the end of the sliding rubber stopper in a syringe can readily be seen with the naked eye and a material with a lower percent photo-transmission can favourably be used for the barrel of the syringe.

Up to the present time, liquid lubricants such as silicone oils have frequently been used to improve the sliding property of a sliding stopper of a syringe, but the liquid lubricant tends to contaminate a liquid medicament used in the syringe and accordingly, it is required to apply to the surface of a rubber base material a solid and lubricating material in such a manner that it is hardly stripped therefrom.

Among known materials capable of satisfying the above described requirement, fluoro-resins have the lowest friction resistance, namely, a friction coefficient of 0.02 to 0.07, whereas PP and PE each has a friction coefficient of 1 to 4. Above all, TFE has the lowest friction coefficient, namely 0.02 to 0.03.

Thus, a TFE film is chosen for the laminating material of a sliding stopper of a syringe, which needs a high sliding property, and it is found that the sliding stopper consisting of a rubber body the surface of which is laminated with a TFE film can give best results and exhibit an excellent initial sliding value without using any silicone oil.

Furthermore, it is found that when the sliding property of the sliding stopper of the present invention is examined by applying it to injection barrels or cylinders of various materials such as glass, PP, PE and polycarbonate, there is also such a problem that it is difficult to visually confirm the position of the end of the sliding stopper in the barrel of the material with a lower transparency such as plastics, although there is no such problem in the case of using a transparent material such as glass as the material of the barrel. PP and PE each has a lower transparency, namely a percent photo-transmission of 50 to 90% and 10 to 80% respectively. This is due to the fact that since TFE is intrinsically milk white, the laminated part becomes mil white and there is no contrast difference between the laminated part and barrel.

The inventors have succeeded in solving this problem by laminated a sliding stopper with a colored TFE film to give a contrast difference between the TFE film and barrel. As a coloring agent for coloring TFE, there can be used any material which is capable of giving a strong contrast by its color without having any injurious action on a human body and without elution in liquid medicaments, for example, ultramarine blue, carbon black, red oxide and the like. On the other hand, the use of a colored rubber material laminated with a milk white TFE film is not preferable because the black of rubber is not clear and a color unevenness appears on the shaped article.

The base of the TFE laminated sliding stopper according to the present invention is made of a rubber or elastomeric material selected from synthetic rubbers or natural rubbers, for example, isoprene, butadiene, styrene-butadiene, ethylene-propylene, isoprene-isobutylene and nitrile rubbers and the like. These rubbers are generally blended with filler and bridging agents in conventional manner.

Lamination of the TFE film according to the present invention is generally carried out by the method described in Japanese Patent Publication No. 53184/1982, incorporated herein by reference, which the inventors have proposed. The thickness of the laminated TFE film is generally in the range of 0.010 to 0.2 mm, preferably 0.010 to 0.1 mm, since if it exceeds 0.2 mm, the laminated operation is easy, but the sealing property is lowered because of the increased hardness.

Embodiments of the sliding stopper for a syringe according to the present invention will now be illustrated with reference to the accompanying drawings:

FIG. 1 is a cross-sectional view of one embodiment of the present invention, in which a sliding stopper 3 of the present invention consisting of a rubber base material 5 is laminated with a TFE film 7 as a surface 11 to be contacted with a liquid medicament 8 and a sliding surface 10 on the inner wall of a barrel 1 is used in a syringe of disposal type, comprising a barrel 1, plunger rod 2, needle 4 and support recess 6.

FIG. 2 is a cross-sectional view of another embodiment of the present invention, in which a syringe additionally serving as a container 1 is filled with a liquid medicament 8 and sealed by a sliding stopper 3 of the present invention, which are just ready to be engaged with an auxiliary means 9 of the syringe. When using this syringe, the auxiliary means 9 is screwed in a threaded part 6' of the sliding stopper 3 to allow a duplex head needle 4' to penetrate into the sliding stopper and further thrust to move the stopper 3 to the right in FIG. 2, whereby the corresponding quantity of the liquid medicament 8 is flowed out into the duplex head needle 4', reaching the needle 4.

Figure 3:
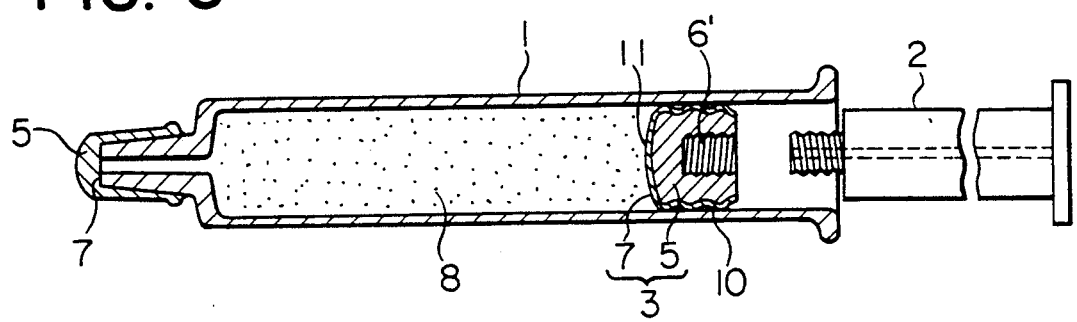
FIG. 3 is a cross-sectional view of a further embodiment of the laminated rubber stopper of the present invention when applied to a syringe additionally serving as a container for a liquid medicament.

FIG. 3 is a cross-sectional view of a further embodiment of the present invention, in which a syringe barrel 1 is filled with a liquid medicament 8 and sealed by a sliding stopper 3 of the present invention. When using this syringe, a plunger rod 2 is screwed in a threaded part 6' of the sliding stopper 3.

Figure 4:
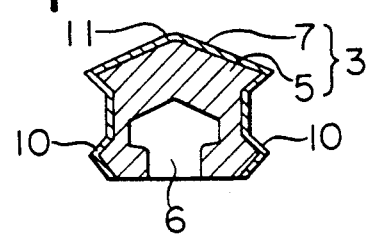
FIG. 4 and FIG. 5 are cross-sectional views of preferred embodiments of the sliding rubber stopper of the present invention.
Figure 5:
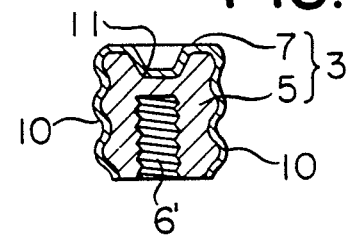

FIG. 4 and FIG. 5 are cross-sectional views of sliding stoppers of the present invention, respectively used in the embodiments of FIG. 1 and FIG. 2, in each of which the rubber base material 5 is fully laminated with the TFE film 7 at the part 11 to be contacted with a liquid medicament and the sliding part 10 on the inner wall of the barrel 1.

In the sliding stopper 3 of the present invention as shown in FIG. 1 to FIG. 5, a colored TFE can of course be used as the laminated part 7 depending on the material of the syringe barrel 1.

Figure 6:
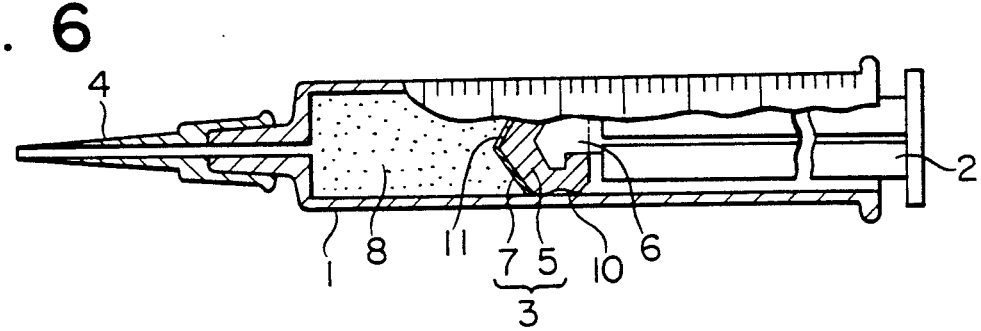
FIG. 6 is a cross-sectional view of one example of a sliding stopper of the prior art, whose only part to be contacted with a liquid medicament is laminated with a fluoro-resin.

FIG. 6 is a cross-sectional view of a sliding stopper 3 of the prior art, in which a TFE film 7 is laminated on only a part 11 to be contacted with a liquid medicament 8 to retain the rubber surface exposed at a sliding part 10 on the inner wall of the barrel 1.

The sliding stopper of the present invention has the following advantages:

(1) In all of commercially available syringes, silicone oils are used to improve the sliding property. According to the present invention, however, the use of the silicone oil is not required and contamination of a liquid medicament with foreign matters during injecting can be prevented to a greater extent.

(2) Since the quantity of materials dissolved out of the sliding stopper is largely reduced, the sliding stopper can be applied to a syringe additionally serving as a container for a liquid medicament with such an advantage that the quality of the liquid medicament can be maintained for a long time as it is, when the liquid medicament was prepared.

(3) Since knocking due to the coating unevenness of a silicone oil in a syringe can be prevented, it is possible to administer precise doses of a medicament.

(4) Deairing can favorably be carried out and the deairing operation time from aspiration of a liquid medicament in a syringe to dosing of the medicament can be shortened. Thus, there is little danger of misinjection of air in a human body.

(5) Even if a barrel is of a semitransparent material, the movement and position of the sliding stopper can readily be confirmed by coloring the TFE film, in particular, in black.

The following examples are given in order to illustrate the present invention in greater detail without limiting the same.

Preliminary Test

Comparison of the sliding resistances of TFE-, Pe- and PP- laminated sliding stoppers Rubber Composition

| | |
|---|---|
| Polybutadiene Rubber (JSR BR 01 -commercial name- made by Japan Synthetic Rubber Co.) | 80 parts |
| Polyisoprene Rubber (Nipol 2200 -commercial name- made by Nippon Zeon Co.) | 20 parts |
| Wet Process Silica (Carplex 1120 -commercial name- made by Shionogi Seiyaku Co.) | 15 parts |
| Calcined Clay (Burgess Iceberg -commercial name- made by Burgess Pigment Co.) | 20 parts |
| Carbon Black (Asahi Carbon No. 35 -commercial name- made by Asahi Carbon Co.) | 5 parts |
| Low Molecular Weight Polyethylene (HI-WAX No. 110 P -commercial name- made by Mitsui Sekiyu Kagaku Co.) | 2 parts |
| $\alpha,\alpha'$-bis(t-butylperoxy-m-isopropyl)benzene (Perbutyl p -commercial name- Nippon Yushi Co.) | 1.5 parts |

Material of Laminating Film

TFE Film: Neoflon TFE ®—commercial name—made by Daikin Kogyo Co., 75 um thickness, one side etched by sputtering Polyethylene Film: Sholex ®—commercial name—made by Showa Denko Co. 75 um thickness Polypropylene Film: Mitsui Polypro ®—Commercial name—made by Mitsui Sekiyu Kagaku Co., 75 um thickness The rubber composition with the above described formulation was kneaded using two rolls for rubber according to the "Rubber Test Method" by the Society of Rubber Industry, Japan. The resulting nonvulcanized rubber was shaped into a sheet on which each of the above described laminating films was superimposed in such a manner that the sputtered surface of the film was contacted with the rubber, placed on a lower metal mold having a recess corresponding to the shape of the sliding stopper shown in FIG. 4 in such a manner that the film surface was contacted with the mold and then molded by heating at a temperature of 165 to 185° C. and a pressure of 50 to 100 kg/cm² for 7 hours by the use of an upper metal mold having a projection corresponding to the recess 6 of the sliding stopper 3. The thus molded article was then subjected to punching to remove the burr formed round it and washed with warm water, thus obtaining a laminated sliding stopper. The whole surface of a part of the stopper to be contacted with a liquid medicament and another part sliding on the inner surface of a barrel was fully laminated with the film.

Sliding Test

The resulting sliding stopper was inserted into a barrel of a syringe made of PP at the maximum scale mark (6 ml) and then subjected to measurement of a drawing resistance using Shimadzu Autograph DCS-100 (commercial name, made by Shimadzu Seisakujo Co.), thus attaining an initial value as a statical friction force and a sliding value as a knetic friction force, as shown in Table 1:

TABLE 1

| Kind of Laminating Film | Initial Value (g) | Sliding Value (g) |
|---|---|---|
| TFE | 230–240 | 120–140 |
| PE | 12000–14000 | 11000–12000 |
| PP | 9000–10000 | 7000–8000 |

As is evident from these results, the TFE film laminated sliding stopper gives a very small initial value and sliding value of the absence of a silicone oil.

EXAMPLE 1

Rubber Composition

| | |
|---|---|
| Polybutadiene Rubber (Nipol BR -commercial name-, made by Nippon Zeon Co.) | 68 wt % |
| Polyisoprene Rubber (Nipol IR -commercial name-, made by Nippon Zeon Co.) | 2.7 wt % |
| Reinforcing Agent | 24.1 wt % |
| Organic Crosslinking Agent | 1.8 wt % |

The procedures of the Preliminary Test were repeated except using the above described rubber composition to obtain a TFE laminated sliding stopper, as shown in FIG. 4, which was then subjected to various tests described below, thus obtaining results as shown in Table 2.

EXAMPLE 2

Example 1 was repeated except using a black-colored TFE film as the TFE laminating film to obtain a TFE laminated sliding stopper with the same shape as that of Example 1. In this case, the coloring was carried out by mixing a finely powdered TFE with 5% by weight of carbon black, sintering the mixture and then subjecting to a skiving treatment to obtain a colored TFE film. The resulting sliding stopper was then subjected to the same tests, thus obtaining results shown in Table 2.

COMPARATIVE EXAMPLE 1

Example 1 was repeated except laminating the part to be contacted with a liquid medicament and only a part of the sliding part as shown in FIG. 6 with a TFE film (not colored) to obtain a sliding stopper for comparison, which was then subjected to the same tests, thus obtaining results shown in Table 2.

COMPARATIVE EXAMPLE 2

Example 1 was repeated except laminating the whole surface of the part to be contacted with a liquid medicament and the sliding part with a PP film (not colored) to obtain a sliding stopper for comparison, which was then subjected to the same tests, thus obtaining results shown in Table 2.

COMPARATIVE EXAMPLES 3 to 6

Commercially available stoppers A, B, C and D, not laminated, were subjected to the same tests, thus obtaining results shown in Table 2.

In Table 2, "ND" means an amount than lower the limit which can be detected.

TEST METHODS

(1) Legal Tests I to IV

Test I to III: Notification No. 442 of the Welfare Ministry, Standard for Syringe Barrel of Disposal Type Test IV: Test Method of Rubber Stopper for Liquid Transfusion according to 11th Revision,

JAPANESE PHARMACOPOEIA

Test I

Elution test with water (70° C.×30 min.) to determine (i) the outward appearance, (ii) pH, and the amounts of (iii) heavy metals, (iv) potassium permanganate reducing materials and (v) evaporation residues

Test II

Elution test with a solvent such as trifluorotrichloroethane to determine the amount of silicone oil dissolved out (n=20)

In each Example, 20 samples were subjected to this test to determine quantitatively silicone oil used in a syringe using trifluorotrichloroethane.

Test III

Physical tests including (i) pressure test, (ii) aspiration test and (iii) movement test

Test IV

Elution or Extraction test to determine (i) pH, (ii) percent transmission of visible rays, (iii) ultraviolet absorption spectrum and (iv) potassium permanganate reducing materials.

(2) Independent Tests V and VI

Test V

Physical tests including (i) sliding test, (ii) knocking test and (iii) deairing test

(i) Sliding Test

When a syringe barrel to which an injection needle is not attached is fixed and a plunger rod is thrust to move a sliding stopper, the load (initial value and sliding value) is measured in an analogous manner to the Preliminary Test.

(ii) Knocking Test (Fluctuation of Sliding Value)

"Good" means such a state that when a plunger rod is thrust in a syringe barrel, it is moved in smooth and continuous manner, while "knocking" means such a state that the plunger rod is intermittently moved. The knocking property is an important property dosed as predetermined or not.

(iii) Deairing Test

After purified water is aspirated in a syringe to the maximum scale mark and then discharged by 1 ml by thrusting the plunger under such a state that the needle is directed upward, the presence or absence of bubbles is visually examined. Mark ○ shows bubble-free state and mark x shows a bubbled state.

Test VI

Test VI is a fine particle test effected by aspirating 5 ml of purified water by a syringe, discharging the water by thrusting and collecting, repeating this procedure three times to obtain a test liquid and after allowing to stand for 30 minutes, subjected 12 ml of the test liquid to measurement using an optical fine particle tester (RION). In each Example, 20 samples were used and subjected to this test and the results are shown in Table 2 as mean values per one sample.

The general assessment of the results is represented by "Very Good"◎, "Normal" Δ and "Unsuitable" X.

TABLE 2

| | | | Example | | | | Comparative Example | | | | | |
|---|---|---|---|---|---|---|---|---|---|---|---|---|
| | | Test Items | Example 1 Present Invention TFE whole | Example 2 Present Invention (colored) Colored TFE whole | Comparative Example 1 Comparison TFE Only TFE End | Comparative Example 2 Comparison PP whole | Comparative Example 3 Commercially Available Article A Laminating Sample | Comparative Example 4 Commercially Available Article B | Comparative Example 5 Commercially Available Article C | Comparative Example 6 Commercially Available Article D | | Stand |
| Legal Test I to III | I | (i) Appearance | ○ | ○ | ○ | ○ | ○ | ○ | ○ | ○ | No | Color clear foreign matte |
| | | (ii) pH | +0.02 | +0.02 | +0.04 | 0.1 | +0.30 | +0.25 | +0.30 | +0.04 | | <2.0 |
| | | (iii) Heavy Metals | ND | ND | ND | ND | ND | ND | ND | ND | | <2 pp |
| | | (iv) KMnO4 Reducing Materials | 0.05 ml | 0.06 ml | 0.08 ml | 0.1 ml | 0.23 ml | 0.31 ml | 0.25 ml | 0.12 ml | | <2 ml |
| | | (v) Evaporation Residues | ND | ND | ND | ND | 0.7 mg | 2.2 mg | 0.8 mg | 0.8 mg | | <1.0 |
| | II | Elution with Trifluorotrichloroethane (Silicone Oil) | ND | ND | ND | ND | x̄ = 4985 μg max = 5380 μg min = 3730 | x̄ = 3823 μg max = 4800 μg min = 3430 | x̄ = 3903 μg max = 5100 μg min = 3180 | x̄ = 3212 μg max = 4320 μg min = 2900 | | 5 m |
| | III | (i) pressure Test | suitable | suitable | suitable | unsuitable | suitable | suitable | suitable | suitable | | |
| | | (ii) Aspiration Test | suitable | suitable | suitable | unsuitable | suitable | suitable | suitable | suitable | | |
| | | (iii) Movement Test | suitable | suitable | unsuitable | unsuitable | suitable | suitable | suitable | suitable | | |
| Legal Test IV | IV | (i) pH | -0.25 | -0.28 | -0.45 | -0.35 | +1.12 | +2.05 | +2.73 | +0.59 | | |
| | | (ii) Percent Transmission of Visible Rays | | | | | | | | | | |
| | | VR 430 Nm | 99.9% | 99.9% | 99.8% | 99.8% | 99.4% | 88.0% | 80.8% | 99.8% | | >99.0% |
| | | 650 Nm | 100.0% | 100.0% | 100.0% | 99.9% | 99.7% | 93.1% | 89.9% | 100.0% | | >99.0% |
| | | (iii) UV Absorption Spectrum 220-1350 Nm | 0.012 | 0.014 | 0.025 | 0.032 | 0.105 | 0.760 | 1.256 | 0.036 | | less than 0.2 absorbance |
| | | (iv) KMnO4 Reducing Materials (OXD) | 0.41 ml | 0.45 ml | 0.90 ml | 0.8 ml | 1.80 ml | 26.10 ml | 31.20 ml | 1.91 ml | | <2.0 ml |
| | V | Sliding Test Initial Value | 230 g | 240 g | 10 kg | 9.5 kg | 780 g | 930 g | 850 g | 600 g | | |
| | | Sliding Test Sliding Value | 120 g | 140 g | | 7.7 kg | 410 g | 390 g | 420 g | 330 g | | |
| | | Knocking Property | good | good | knocking | knocking | some knocking | some knocking | some knocking | some knocking | | |
| | | Deairing Property | ○ | ○ | ○ | ○ | x | x | x | x | | |

TABLE 2-continued

| | | Example 1 | Example 2 | Comparative Example 1 | Comparative Example 2 | Comparative Example 3 Sample | Comparative Example 4 | Comparative Example 5 | Comparative Example 6 |
|---|---|---|---|---|---|---|---|---|---|
| Test Items | | Present Invention TFE whole | Present Invention (colored) Colored TFE whole | Comparison TFE Only TFE End | Comparison PP whole | Commercially Available Article A Laminating | Commercially Available Article B | Commercially Available Article C | Commercially Available Article D |
| Tests V and VI | VI Fine Particles 2μ | 183 | 230 | | | 6581 | 5195 | 5036 | 3510 |
| | 5μ | 49 | 58 | | | 2200 | 1729 | 1669 | 1230 |
| | 10μ | 5 | 15 | | | 430 | 382 | 402 | 165 |
| | 20μ | 0 | 0 | | | 150 | 103 | 162 | 30 |
| | 30μ | 0 | 0 | | | 25 | 15 | 48 | 4 |
| General Assessment | | ◎ | ◎ | × | × | △ | △ | △ | △ |
| | | | | | | No | No | No | No Stand |

Test Results

Test results shown in Table 2 are summarized below:

I. Elution Test with Water

There is a great difference between the laminated samples of Examples 1 and 2, and Comparative Examples 1 and 2, and the non-laminated samples of Comparative Examples 3 to 6. As to the Evaporation Residues, in particular, Comparative Examples 3 to 6 give values near the standard or exceeding it (Comparative Example 4).

II. Elution Test with Solvent

Silicone oil cannot be found in the laminated samples, but a considerable amount of silicone oil exceeding the standard value is determined in the non-laminated samples.

III. Physical Test

All the samples except those of Comparative Examples 1 to 2 satisfy the standard. In Comparative Examples 1 and 2, silicone oil was not used and accordingly, the sliding property of the stopper was worse. In Examples 1 and 2 according to the present invention, on the other hand, silicone oil was not used, but good results were given.

IV. Elution or Extraction Test

Since this elution test is carried out under severer conditions than the Elution Tests I and II, there is a clearer difference between the stoppers of Examples 1 and 2 according to the present invention and Comparative Examples.

V. Physical Test (Independent Test)

The movement load test is a test assuming the condition that a syringe is readily used. Examples 1 and 2 show more excellent results concerning the sliding property as compared with Comparative Examples. The stoppers of Comparative Examples 1 and 2 are not suitable for practical use, since the sliding property is worse unless silicone oil is used. In the knocking test, the stoppers of Examples 1 and 2 doe not exhibit knocking, but those of Comparative Examples exhibit knocking, more or less. This is probably due to partial coating unevenness of silicone oil on the inner wall of a syringe barrel and the plunger part. In the deairing test, more bubbles are found in the case of using a large quantity of silicone oil.

VI. Fine Particle Test

This test teaches that the stoppers of the present invention give much less fine particles of foreign matters and in particular, those with a particle size of about 2 $\mu$m can be decreased to 1/35 of the prior art according to the present invention. Furthermore, fine particle foreign matters with a particle size of at least 20 $\mu$m cannot be found in the present invention.

As a general estimation, the sliding stoppers of the present invention can favorably be compared with the comparative samples in all the Tests I to VI.

What is claimed is:

1. A sliding stopper for a syringe, consisting of a rubber elastic body whose part to be contacted with a liquid medicament and sliding part on an inner wall of a barrel are fully laminated with a film of tetrafluoroethylene.

2. The sliding stopper as claimed in claim 1, wherein the film of tetrafluoroethylene has a thickness of 0.01 to 0.2 mm.

3. The sliding stopper as claimed in claim 1, wherein the syringe additionally serves as a container for a medicament.

4. The sliding stopper as claimed in claim 1, wherein the film of tetrafluoroethylene is colored.

5. The sliding stopper as claimed in claim 4, wherein the coloring is carried out by the use of a coloring agent selected from the group consisting of ultramarine blue, carbon black and red oxide.

6. The sliding stopper as claimed in claim 1, wherein the rubber elastic body is made of a rubber or elastic material selected from the group consisting of isoprene, butadiene, styrene-butadiene, ethylene-propylene, isoprene-isobutylene and nitrile rubbers.

* * * * *